United States Patent
Imamura et al.

(10) Patent No.: US 6,624,146 B1
(45) Date of Patent: Sep. 23, 2003

(54) PHARMACEUTICAL COMPOSITIONS CONTAINING FIBROBLAST GROWTH FACTOR-RELATED PEPTIDES

(75) Inventors: Toru Imamura, Tokyo (JP); Ai-Jun Li, Ibaraki (JP); Akiko Kuramochi, Ibaraki (JP); Hiroyuki Tsuboyama, Tochigi (JP)

(73) Assignee: Agency of Industrial Science and Technology, Tokyo (JP)

( * ) Notice: Subject to any disclaimer, the term of this patent is extended or adjusted under 35 U.S.C. 154(b) by 0 days.

(21) Appl. No.: 09/720,039

(22) PCT Filed: Mar. 31, 1999

(86) PCT No.: PCT/JP99/01697

§ 371 (c)(1), (2), (4) Date: Apr. 4, 2001

(87) PCT Pub. No.: WO99/65512

PCT Pub. Date: Dec. 23, 1999

(30) Foreign Application Priority Data

Jun. 19, 1998 (JP) .............................. 10-172325

(51) Int. Cl.⁷ .......................... A61K 38/00; C07K 7/00; C07K 14/00
(52) U.S. Cl. .............................. 514/12; 514/2; 514/13; 530/300
(58) Field of Search ............................... 514/2, 12, 13; 530/300

(56) References Cited

U.S. PATENT DOCUMENTS 6,045,793 A * 4/2000 Rybak et al. .............. 424/94.6

FOREIGN PATENT DOCUMENTS

| JP | 7-291859 A | | 11/1995 |
|---|---|---|---|
| JP | 7-291860 A | | 11/1995 |
| JP | 10-87491 A | | 4/1998 |
| WO | WO 96/06641 | * | 3/1996 |
| WO | WO 97/09877 A1 | | 3/1997 |
| WO | WO 97/30712 A1 | | 8/1997 |
| WO | WO 98/09620 A1 | | 3/1998 |

OTHER PUBLICATIONS

Lin YZ et al., "Inhibition of nuclear translocation of transcription factor NF–kappa B by a synthetic peptide containing a cell membrane–permeable motif and nuclear localization," *J. Bio. Chem.*, vol. 270, No. 24, 1995, pp. 14255–14258.

* cited by examiner

*Primary Examiner*—Gary Kunz
*Assistant Examiner*—Regina M. DeBerry
(74) *Attorney, Agent, or Firm*—Fish & Richardson P.C.

(57) ABSTRACT

The present invention relates to a pharmaceutical composition comprising, as an active ingredient, a peptide represented by the following formula (I):

$$\text{MTS-X-NLS} \qquad (I)$$

wherein MTS represents a membrane-transfer amino acid sequence; X represents a direct bond or a linker sequence; and NLS represents a nuclear localization amino acid sequence, or a pharmaceutically acceptable salt thereof, particularly, a pharmaceutical composition having food and water intake inhibitory effects, and accompanying weight-reducing and obesity-inhibiting effects.

2 Claims, No Drawings

SEQUENCE LISTING

<160> NUMBER OF SEQ ID NOS: 3

<210> SEQ ID NO 1
<211> LENGTH: 16
<212> TYPE: PRT
<213> ORGANISM: Artificial Sequence
<220> FEATURE:
<223> OTHER INFORMATION: Derivative of partial peptide of fibroblast
      growth factors

<400> SEQUENCE: 1

Ala Ala Val Ala Leu Leu Pro Ala Val Leu Leu Ala Leu Leu Ala Val
1               5                   10                  15

<210> SEQ ID NO 2
<211> LENGTH: 7
<212> TYPE: PRT
<213> ORGANISM: Artificial Sequence
<220> FEATURE:
<223> OTHER INFORMATION: Derivative of partial peptide of fibroblast
      growth factors

<400> SEQUENCE: 2

Asn Tyr Lys Lys Pro Lys Leu

```
                1                 5

<210> SEQ ID NO 3
<211> LENGTH: 26
<212> TYPE: PRT
<213> ORGANISM: Artificial Sequence
<220> FEATURE:
<223> OTHER INFORMATION: Derivative of partial peptide of fibroblast
      growth factors

<400> SEQUENCE: 3

Ala Ala Val Ala Leu Leu Pro Ala Val Leu Leu Ala Leu Leu Ala Val
 1               5                  10                  15

Ala Ala Ala Asn Tyr Lys Lys Pro Lys Leu
            20                  25
```

PHARMACEUTICAL COMPOSITIONS CONTAINING FIBROBLAST GROWTH FACTOR-RELATED PEPTIDES

CROSS-REFERENCE TO RELATED APPLICATIONS

This application claims the benefit of priority under 35 U.S.C. §371 to the PCT International Application PCT/JP99/01697, filed Mar. 31, 1999, published Dec. 23, 1999 as WO 99/65512, in Japanese; which claims priority to Japanese Application No. 172325/1998, filed Jun. 19, 1998. All applications are incorporated by reference in their entirety and for all purposes.

FIELD OF THE INVENTION

The present invention relates to pharmaceutical compositions comprising a peptide derived from fibroblast growth factor as an active ingredient.

BACKGROUND OF THE INVENTION

Some Fibroblast Growth Factors (called FGF hereinafter) are known to have various physiological activities, and a variety of studies have been made with the expectation of their use as pharmaceuticals. A food intake inhibitory effect is known to be one of the physiological activities of FGF. The FGF that is released from ependymocytes of the cerebral ventricle wall by responding to a glucose concentration in the brain, is considered to act on neurons of the feeding center in the brain repressively, resulting in the food intake inhibitory and weight-reducing effects.

Since FGF is a protein comprising one hundred and several tens of amino acids, however, there were the following problems with its use, as is, as a pharmaceutical: 1) the synthesis of FGF is difficult; 2) immunological rejection occurs in vivo; 3) administration methods are limited; 4) it is difficult to conserve FGF without causing changes of the active three-dimensional structure.

Therefore, there are strong demands on development of medicaments comprising FGF with physiological activity, particularly, food intake inhibitory effect, without any of the above problems.

DISCLOSURE OF THE INVENTION

An object of the present invention is to provide a pharmaceutical composition having physiological activity, particularly, food intake inhibitory effect of FGF and having no problems that occurs when FGF is used directly as a medicament.

The inventors have studied extensively and intensively to solve above problems and have now found that a partial peptide derivative, Ala-Ala-Val-Ala-Leu-Leu-Pro-Ala-Val-Leu-Leu-Ala-Leu-Leu-Ala-Val-Ala-Ala-Ala-Asn-Try-Lys-Lys-Pro-Lys-Leu (SEQ ID NO:3) (Lin Y. Z. et al., J. Biol. Chem., 270, 14255–14258 (1995), of an FGF previously known to have superior cell membrane transfer and cell nuclear membrane transfer, unexpectedly has strong food and water intake inhibitory effects. The inventors have further found based on this finding that the peptide which is obtained by combining a peptide with cell membrane transfer and a peptide with cell nuclear localization has strong food and water intake inhibitory effects, and accompanying weight-reducing and obesity-inhibiting effects, thereby completing the present invention.

Thus, the present invention comprises the following inventions:

(1) A pharmaceutical composition comprising a peptide represented by the following formula (I):

$$\text{MTS-X-NLS} \tag{I}$$

wherein MTS represents a membrane-transfer amino acid sequence; X represents a direct bond or a linker sequence; and NLS represents a nuclear localization amino acid sequence, or a pharmaceutically acceptable salt thereof as an active ingredient.

(2) The pharmaceutical composition of (1) above, wherein the MTS is represented by the following amino acid sequence:
 (a) an amino acid sequence of SEQ ID NO:1; or
 (b) an amino acid sequence comprising deletions, substitutions or additions of one or more amino acid residues relative to the amino acid sequence of SEQ ID NO: 1.

(3) The pharmaceutical composition of (1) or (2) above, wherein the NLS is represented by the following amino acid sequence:
 (a) an amino acid sequence of SEQ ID NO:2; or
 (b) an amino acid sequence comprising deletions, substitutions or additions of one or more amino acid residues relative to the amino acid sequence of SEQ ID NO:2.

(4) The pharmaceutical composition of any one of (1) to (3) above, wherein the pharmaceutical composition is for inhibition of food intake.

(5) The pharmaceutical composition of any one of (1) to (3) above, wherein the pharmaceutical composition is for inhibition of water intake.

(6) The pharmaceutical composition of (4) above, having a weight-reducing and/or obesity-inhibiting effect.

(7) The pharmaceutical composition of (5) above, having a weight-reducing and/or obesity-inhibiting effect.

The present invention will be described in detail as follows.

A pharmaceutical composition of the present invention is characterized in that it comprises, as the active ingredient, a peptide represented by the following formula (I):

$$\text{MTS-X-NLS} \tag{I}$$

where MTS represents a membrane-transfer amino acid sequence; X represents a direct bond or a linker sequence; and NLS represents a nuclear localization amino acid sequence, or a pharmaceutically acceptable salt thereof.

As used herein, the term "membrane-transfer amino acid sequence" represented by MTS means an amino acid sequence corresponding to a peptide with cell membrane transfer properties, and the term "nuclear localization amino acid sequence" represented by NLS means an amino acid sequence corresponding to a peptide with nuclear localization properties.

MTS may be any amino acid sequence as long as it is a membrane-transfer amino acid sequence, but particularly preferred is the amino acid sequence of SEQ ID NO: 1 or an amino acid sequence comprising deletions, substitutions or additions of one or more amino acid residues relative to the amino acid sequence of SEQ ID NO: 1.

As used herein, the term "one or more amino acid residues" does not limit the number thereof so far as the cell membrane transfer of a peptide corresponding to the amino acid sequence is not lost.

The number of amino acid residues is, but not limited to, normally 7–40, preferably 16.

The NLS may be any amino acid sequence as long as it is a nuclear localization amino acid sequence, but particularly preferred is the amino acid sequence according to SEQ ID NO:2 or an amino acid sequence comprising deletions, substitutions or additions of one or more amino acid residues relative to the amino acid sequence of SEQ ID NO:2.

As used herein, the term "one or more amino acid residues" does not limit the number so long as the nuclear localization of a peptide corresponding to the amino acid sequence is not lost.

The number of amino acid residues is, but not limited to, normally 3–15, preferably 4–7.

In the formula (I), X represents a direct bond or a linker sequence. MTS and NLS may be bound together directly, or otherwise, a linker sequence may intervene between MTS and NLS. The linker sequence includes, for example, amino acid sequences comprising one or more Ala or Gly residues, or combination thereof. The number of amino acid residues in the linker sequence is, but not limited to, normally 1–20, preferably 2–7.

The peptide represented by the formula (I) includes for example peptides in which MTS is located on the N-terminal side while NLS on the C-terminal side, and peptides in which MTS is located on C-terminal side while NLS on the N-terminal side.

The number of the amino acid residues represented by the formula (I) is, but not limited to, normally 10–40, preferably 23–27.

The peptides represented by the formula (I) can be chemically synthesized, for example, by known peptide synthesis methods.

Examples of peptide synthesis methods include azide, acid chloride, acid anhydride, mixed acid anhydride, DCC, activated ester, carboimidazole, oxidation-reduction, and DCC-additive (HONB,HOBt,HOSu) methods. (Schreder and Luhke "The Peptide" Vol.1 (1996), Academic Press, N.Y., USA; Izumiya et al., "Peptide Synthesis", Maruzen Inc. (1975)). These peptide synthesis methods can be carried out either by a solid phase synthesis or a liquid phase synthesis.

Examples of pharmaceutically acceptable salts of peptide which is represented by the formula (I) include sodium or hydrochloride salts.

As the pharmaceutical composition of the present invention, peptides represented by the formula (1) or pharmaceutically acceptable salts thereof may directly be used as they are, or alternatively they may be formulated in combination with pharmaceutically acceptable carriers.

Examples of pharmaceutically acceptable carriers include excipients such as fillers, extenders, binders, humectants, disintegrating agents and surfactants; or diluents, which are commonly used for preparing formulations depending on usage forms. The dosage form of the pharmaceutical composition of the present invention can include, but not limited to, e.g. tablets, powders, granules, and pills, or solutions, suspensions and emulsions, so far as it effectively contains a peptide represented by the formula (I). Furthermore, the pharmaceutical composition of the present invention may be dry forms capable of changing into a liquid form by addition of a proper carrier before use. The formulation can be carried out in a usual manner.

Dose of the pharmaceutical composition of the present invention is appropriately selected depending on administration methods, dosage forms, or conditions of a patient to be administered, or the like. Generally, it is appropriate to prepare a formulation comprising a peptide of the invention at a rate of about 1–100% by weight, and to administer the peptide contained in the formulation in a dose of about 0.2–300 mg per day per adult person. Furthermore, the administration is not necessarily given once a day, but can be divided over several times a day.

The pharmaceutical composition of the invention can be administered via an administration route which depends on dosage forms. For example, in the case of an injection form, administration can be intravenous, intramuscular, subcutaneous, intracutaneous, or intraperitoneal, and in the case of a solid form, administration can be done perorally, etc.

The pharmaceutical composition of the invention has food and water intake inhibitory effects, as well as weight-reducing and obesity-inhibiting effects. Hence, the administration of the pharmaceutical composition of the invention results in food and water intake inhibitory effects, and accompanying weight-reducing and obesity-inhibiting effects, indicating that the composition is particularly useful for diseases such as obesity.

The specification incorporates the descriptions in the specification of Japanese Patent Application No. 10-172325 on which the priority of the present application is based.

BEST MODES FOR CARRYING OUT THE INVENTION

Example 1

Weight-reducing Effect

Peptide Ala-Ala-Val-Ala-Leu-Leu-Pro-Ala-Val-Leu-Leu-Ala-Leu-Leu-Ala-Val-Ala-Ala-Ala-Asn-Try-Lys-Lys-Pro-Lys-Leu (SEQ ID NO:3) was synthesized according to Lin Y. Z. et al., J. Biol. Chem. 270, 14255–14258 (1995); Merrifield, R. B. J. Am. Chem. Soc. 85, 2149–2154 (1963); and Lin Y. Z. et al., Biochemistry 27, 5640–5645 (1988). In the amino acid sequence of this peptide, Ala-Ala-Val-Ala-Leu-Leu-Pro-Ala-Val-Leu-Leu-Ala-Leu-Leu-Ala-Val (SEQ ID NO: 1) corresponds to the membrane-transfer amino acid sequence, Ala-Ala-Ala to the linker sequence, and Asn-Try-Lys-Lys-Pro-Lys-Leu (SEQ ID NO:2) to the nuclear localization amino acid sequence, respectively.

This peptide was dissolved in physiological saline to prepare a 2.6 pmol/μl peptide-containing injection solution. Five μl of the injection solution (containing 13 pmol peptide) was administered into the cerebral ventricles of 10-week-old male Wistar rats, which were weighed on the next day to calculate amounts of change in weight prior to and subsequent to injection.

On the other hand, 5 μl physiological saline was administered to rats as a control in the same manner as described above, and 2.6 pmol/μl FGF-containing injection solution was administered to rats as a comparative example in the same manner as described above. Each rat was weighed on the next day to calculate amounts of change in weight prior to and subsequent to injection.

The results are shown in Table 1.

TABLE 1

| Administration substance | dose | Amount of change in weight |
|---|---|---|
| Physiological saline | 5 μl | +2.0g |
| FGF | 13 pmol/5 μl | −10.1g |
| Peptide | 13 pmol/5 μl | −5.3g |

As shown in Table 1, the weights of the rats to which the peptide was administered, were significantly reduced when compared to those of the rats to which the physiological saline as a control was administered. Furthermore, the weights of the rats to which the peptide was administered, were reduced almost equally when compared to those of the rats to which FGF was administered.

From these results, it was demonstrated that the peptide of the invention has a weight-reducing effect.

Example 2

Food and Water Intake Inhibitory Effects

In the same manner as in example 1, the peptide Ala-Ala-Val-Ala-Leu-Leu-Pro-Ala-Val-Leu-Leu-Ala-Leu-Leu-Ala-Val-Ala-Ala-Ala-Asn-Try-Lys-Lys-Pro-Lys-Leu (SEQ ID NO:3) was synthesized. This peptide was dissolved in physiological saline to prepare a 2.6 pmol/µl peptide-containing injection solution. Five µl of the injection solution (containing 13 pmol peptide) was administered in the cerebral ventricles of 10-week old male Wistar rats, and the food and water intake level were measured 12 hours after administration to compare with those in the same period of the day prior to administration.

On the other hand, 5 µl physiological saline was administered as a control in the same manner as described above, and 2.6 pmol/µl FGF-containing injection solution was administered as a comparative example in the same manner as described above. Food and water intake levels were measured respectively 12 hours after administration, and were compared to those in the same period of the day prior to administration to calculate amounts of change in food and water intake.

The results are shown in Table 2.

TABLE 2

| Administration substance | dose | Amount of change in food intake | Amount of change in water intake |
|---|---|---|---|
| Physiological saline | 5 µl | −1.1g | −0.3ml |
| FGF | 13 pmol/5 µl | −6.9g | −12.2ml |
| Peptide | 13 pmol/5 µl | −4.8g | −8.4ml |

As shown in Table 2, food and water intake levels were significantly reduced in the rats to which the peptide was administered when compared to those of the control rats to which the physiological saline was administered. Furthermore, the food and water intake levels of the rats to which the peptide was administered were reduced almost equally when compared to those of the rats to which FGF was administered.

From these results, it was demonstrated that the peptide of the invention has food and water intake inhibitory effects.

All references cited herein are incorporated by reference in their entirety in the present specification.

Industrial Applicability

This invention provides a pharmaceutical composition having food and water intake inhibitory effects, and accompanying weight-reducing and obesity-inhibiting effects. The administration of the pharmaceutical composition of the invention results in food and water intake inhibitory effects, as well as weight-reducing and obesity- inhibiting effects, indicating that the composition is particularly useful for diseases such as obesity.

Furthermore, the pharmaceutical composition of the invention comprises, as an active ingredient, a peptide with superior cell membrane transfer and cell nucleus membrane transfer, and it can be used as a carrier for transporting other drugs to the cytoplasm or cell nuclei.

What is claimed is:

1. A pharmaceutical composition comprising a peptide represented by the following formula (I):

MTS-X-NLS  (I)

wherein said MTS represents a membrane-transfer amino acid sequence and is represented by an amino acid sequence of SEQ ID NO:1; X represents a direct bond or a linker sequence; and said NLS represents a nuclear localization amino acid sequence and is represented by an amino acid sequence of SEQ ID NO:2;
or a pharmaceutically acceptable salt thereof as an active ingredient.

2. A method of reducing food and/or water intake comprising administering a pharmaceutical composition comprising the composition of claim 1, whereby the composition reduces food and/or water intake.

* * * * *